(12) United States Patent
Forsberg et al.

(10) Patent No.: US 12,059,437 B2
(45) Date of Patent: Aug. 13, 2024

(54) METHODS AND COMPOSITIONS FOR HEMATOPOIETIC STEM CELL MOBILIZATION

(71) Applicant: The Regents of the University of California, Oakland, CA (US)

(72) Inventors: Camilla Forsberg, Santa Cruz, CA (US); Stephanie Smith-Berdan, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 437 days.

(21) Appl. No.: 17/065,364

(22) Filed: Oct. 7, 2020

(65) Prior Publication Data

US 2021/0100848 A1    Apr. 8, 2021

Related U.S. Application Data

(60) Provisional application No. 62/912,551, filed on Oct. 8, 2019.

(51) Int. Cl.
| | | |
|---|---|---|
| *A61K 35/28* | (2015.01) | |
| *A61K 31/395* | (2006.01) | |
| *A61K 31/519* | (2006.01) | |

(52) U.S. Cl.
CPC ............ *A61K 35/28* (2013.01); *A61K 31/395* (2013.01); *A61K 31/519* (2013.01)

(58) Field of Classification Search
CPC ..... A61K 35/28; A61K 31/395; A61K 31/519
See application file for complete search history.

(56) References Cited

U.S. PATENT DOCUMENTS

| | | |
|---|---|---|
| 7,897,590 B2 | 3/2011 | Bridger et al. |
| 8,372,797 B2 | 2/2013 | Ichim |
| 9,308,244 B2 | 4/2016 | Singh et al. |
| 2014/0079686 A1 | 3/2014 | Barman et al. |
| 2015/0366943 A1 | 12/2015 | Forsberg et al. |

OTHER PUBLICATIONS

Foresta et al. The PDE5 Inhibitor Sildenafil Increases Circulating Endothelial Progenitor Cells and CXCR4 Expression. J Sex Med 2009;6:369-372 (Year: 2009).*
Shepherd et al. Angiogenic cells can be rapidly mobilized and efficiently harvested from the blood following treatment with AMD3100. Blood. 2006;108:3662-3667 (Year: 2006).*
LiverTox. Clinical and Research Information on Drug-Induced Liver Injury [Internet]. Bethesda (MD): National Institute of Diabetes and Digestive and Kidney Diseases; 2012. Phosphodiesterase Type 5 (PDE5) Inhibitors. [Updated Aug. 2, 2017]. p. (Year: 2017).*
Claesson-Welsh. Vascular permeability-the essentials. Upsala Journal of Medical Sciences. 2015; 120: 135-143 (Year: 2015).*
Domingues et al. New agents in HSC mobilization. Int J Hematol (2017) 105:141-152 (Year: 2017).*
Hoggatt et al. Mobilization of hematopoietic stem cells from the bone marrow niche to the blood compartment. Stem Cell Research & Therapy 2011, 2:13 (Year: 2011).*
Tulpule et al. Severe allergic reaction with anaphylaxis to G-CSF (lenograstim) in a healthy donor. Bone Marrow Transplantation (2009) 44, 129-130 (Year: 2009).*
Andersson, "PDE5 inhibitors-pharmacology and clinical applications 20 years after sildenafil discovery", British journal of pharmacology vol. 175, No. 13, 2018, 2554-2565.
Beaudin et al., "A transient developmental hematopoietic stem cell gives rise to innate-like B and T cells", Cell Stem Cell vol. 19, No. 6, 2016, 768-783.
Bernitz et al., "Granulocyte colony-stimulating factor mobilizes dormant hematopoietic stem cells without proliferation in mice", Blood vol. 129, No. 14, 2017, 1901-1912.
Boyer et al., "All hematopoietic cells develop from hematopoietic stem cells through Flk2/Flt3-positive progenitor cells", Cell stem cell vol. 9, No. 1, 2011, 64-73.
Boyer et al., Clonal and Quantitative In Vivo Assessment of Hematopoietic Stem Cell Differentiation Reveals Strong Erythroid Potential of Multipotent Cells. Stem Cell Reports, 2019, 12, 801-815.
Broxmeyer et al., "Rapid mobilization of murine and human hematopoietic stem and progenitor cells with AMD3100, a CXCR4 antagonist", The Journal of experimental medicine vol. 201, No. 8, 2005, 1307-1318.
Cao et al., "Therapeutic targeting and rapid mobilization of endosteal HSC using a small molecule integrin antagonist", Nature communications vol. 7, No. 1, 2016, 1-13.
Couban et al., "The case for plerixafor to replace filgrastim as the optimal agent to mobilize peripheral blood donors for allogeneic hematopoietic cell transplantation", Experimental hematology 70 (2019): 1-9., 2019, 1-9.
Demirer et al., "Factors influencing collection of peripheral blood stem cells in patients with multiple myeloma", Bone marrow transplantation vol. 17, No. 6, 1996, 937-941.
Devine et al., "Rapid mobilization of functional donor hematopoietic cells without G-CSF using AMD3100, an antagonist of the CXCR4/SDF-1 interaction", Blood, The Journal of the American Society of Hematology vol. 112, No. 4, 2008, 990-998.
Douglas et al., "UK consensus statement on the use of plerixafor to facilitate autologous peripheral blood stem cell collection to support high-dose chemoradiotherapy for patients with malignancy", Journal of clinical apheresis vol. 33, No. 1, 2018, 46-59.
Fitzhugh et al., "Granulocyte colony-stimulating factor (G-CSF) administration in individuals with sickle cell disease: time for a moratorium?", Cytotherapy vol. 11, No. 4, 2009, 464-471.
Gertz et al., "Current status of stem cell mobilization", British journal of haematology vol. 150, No. 6, 2010, 647-662.

(Continued)

*Primary Examiner* — Taeyoon Kim
(74) *Attorney, Agent, or Firm* — Kilpatrick Townsend & Stockton LLP

(57) ABSTRACT

The disclosure is directed to methods for mobilizing hematopoietic stem cells (HSCs) and/or hematopoietic progenitor cells (HPCs) in a subject using sildenafil citrate and AMD3100.

15 Claims, 12 Drawing Sheets

(56) References Cited

OTHER PUBLICATIONS

Giacca et al., "VEGF gene therapy: therapeutic angiogenesis in the clinic and beyond", Gene therapy vol. 19, No. 6, 2012, 622-629.
Giralt et al., "Optimizing autologous stem cell mobilization strategies to improve patient outcomes: consensus guidelines and recommendations", Biology of Blood and Marrow Transplantation vol. 20, No. 3 (2014): 295-308., 2014, 295-308.
Hoggatt et al., "Rapid mobilization reveals a highly engraftable hematopoietic stem cell", Cell vol. 172, No. 1-2, 2018, 191-204.
James et al., "Comparative cost-efficiency analysis of granulocyte colony-stimulating factors for use in chemotherapy patients in the United States", Blood vol. 130, Supplement 1, 2017, 4667.
Jones et al., "Robo4 stabilizes the vascular network by inhibiting pathologic angiogenesis and endothelial hyperpermeability", Nature medicine vol. 14, No. 4, 2008, 448-453.
Keating, "Plerixafor A Review of its Use in Stem-Cell Mobilization in Patients with Lymphoma or Multiple Myeloma", Drugs vol. 71, No. 12, 2011, 1623-1647.
Kikuta et al., "Mobilization of hematopoietic primitive and committed progenitor cells into blood in mice by anti-vascular adhesion molecule-1 antibody alone or in combination with granulocyte colony-stimulating factor", Experimental hematology vol. 28, No. 3, 2000, 311-317.
Körbling et al., "Twenty-five years of peripheral blood stem cell transplantation", Blood vol. 117, No. 24, 2011, 6411-6416.
Leung et al., "The lymphoid-associated interleukin 7 receptor (IL7R) regulates tissue-resident macrophage development", Development vol. 146. No. 14, 2019, dev176180.
Miles et al., "Vascular reactions to histamine, histamine-liberator and leukotaxine in the skin of guinea-pigs", The Journal of physiology vol. 118, No. 2, 1952, 228-257.
Morgan et al., "Predictive factors for successful stem cell mobilization in patients with indolent lymphoproliferative disorders previously treated with fludarabine", Leukemia vol. 18, No. 5, 2004, 1034-1038.
Motta et al., "Effect of Sildenafil on Pre-Eclampsia-Like Mouse Model Induced By L-Name", Reproduction in Domestic Animals vol. 50, No. 4, 2015, 611-616.
Murata et al., "Peripheral blood stem cell mobilization and apheresis: analysis of adverse events in 94 normal donors", Bone marrow transplantation vol. 24, No. 10, 1999, 1065-1071.
Navarro et al., "National marrow donor program session: donor issues", Biology of Blood and Marrow Transplantation vol. 19, No. 1, 2013, S15-S19.
Neben et al., "Mobilization of hematopoietic stem and progenitor cell subpopulations from the marrow to the blood of mice following cyclophosphamide and/or granulocyte colony-stimulating factor", Blood vol. 81, No. 7, 1993, 1960-1967.
Pruijt et al., "Prevention of interleukin-8-induced mobilization of hematopoietic progenitor cells in rhesus monkeys by inhibitory antibodies against the metalloproteinase gelatinase B (MMP-9)", Proceedings of the National Academy of Sciences vol. 96, No. 19, 1999, 10863-10868.
Ramirez et al., "BIO5192, a small molecule inhibitor of VLA-4, mobilizes hematopoietic stem and progenitor cells", Blood vol. 114, No. 7, 2009, 1340-1343.
Shaughnessy et al., "Cost and clinical analysis of autologous hematopoietic stem cell mobilization with G-CSF and plerixafor compared to G-CSF and cyclophosphamide", Biology of Blood and Marrow Transplantation vol. 17, No. 5, 2011, 729-736.
Singh et al., "Neuropeptide Y regulates a vascular gateway for hematopoietic stem and progenitor cells", The Journal of clinical investigation vol. 127, No. 12, 2017, 4527-4540.
Smith-Berdan et al., "Robo4 cooperates with CXCR4 to specify hematopoietic stem cell localization to bone marrow niches", Cell stem cell vol. 8, No. 1, 2011, 72-83.
Smith-Berdan et al., "ROBO4-mediated vascular integrity regulates the directionality of hematopoietic stem cell trafficking", Stem cell reports vol. 4, No. 2, 2015, 255-268.
To et al., "How I treat patients who mobilize hematopoietic stem cells poorly", Blood, The Journal of the American Society of Hematology vol. 118, No. 17, 2011, 4530-4540.
Ugarte et al., "Progressive chromatin condensation and H3K9 methylation regulate the differentiation of embryonic and hematopoietic stem cells", Stem cell reports vol. 5, No. 5, 2015, 728-740.

\* cited by examiner

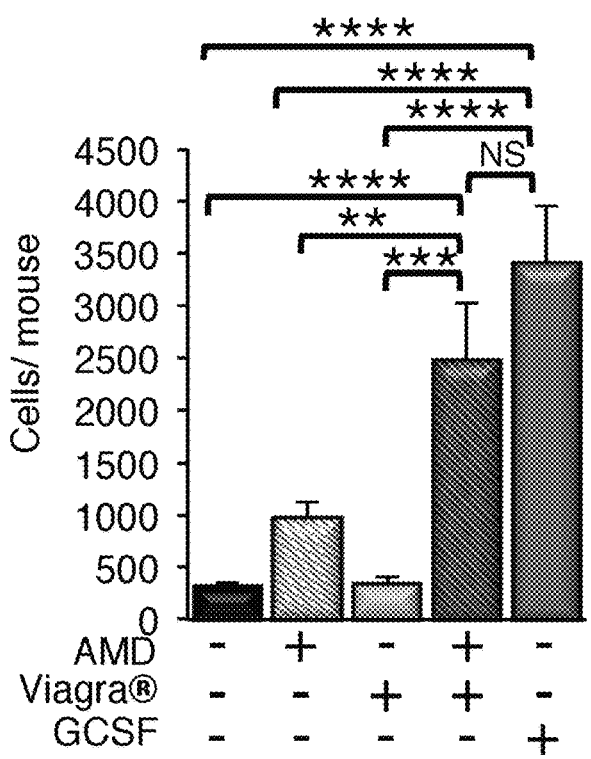

Permeability Assay

% Donor in PB (Lethal)

FIG. 1G Lineage PB

FIG. 1H Donor HSC

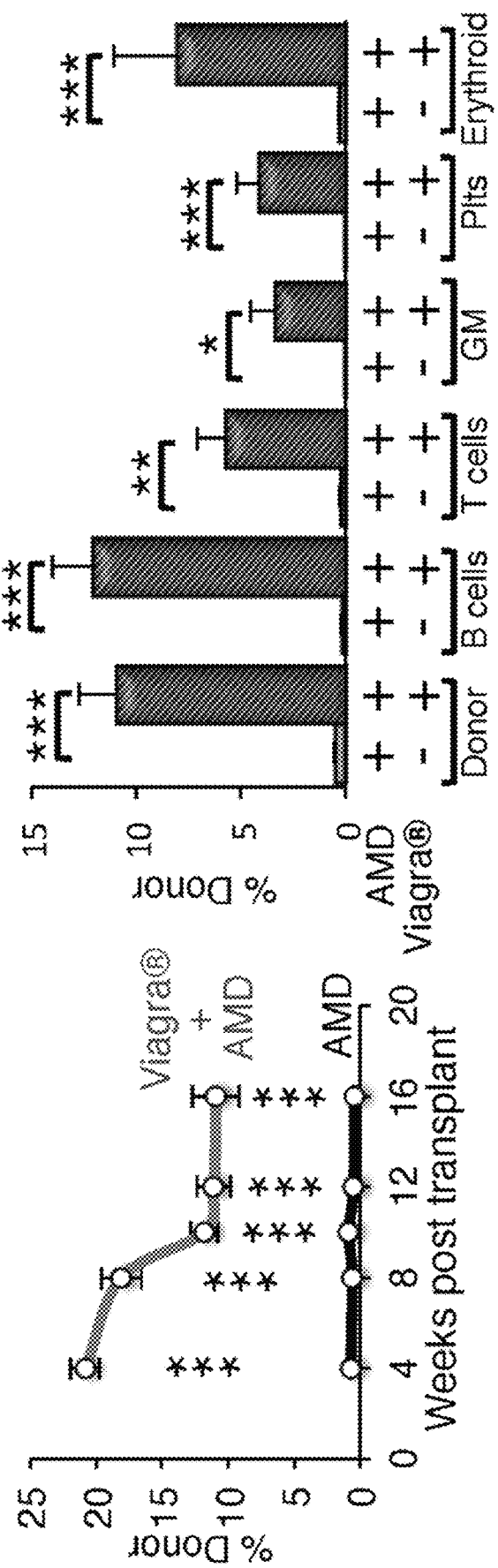

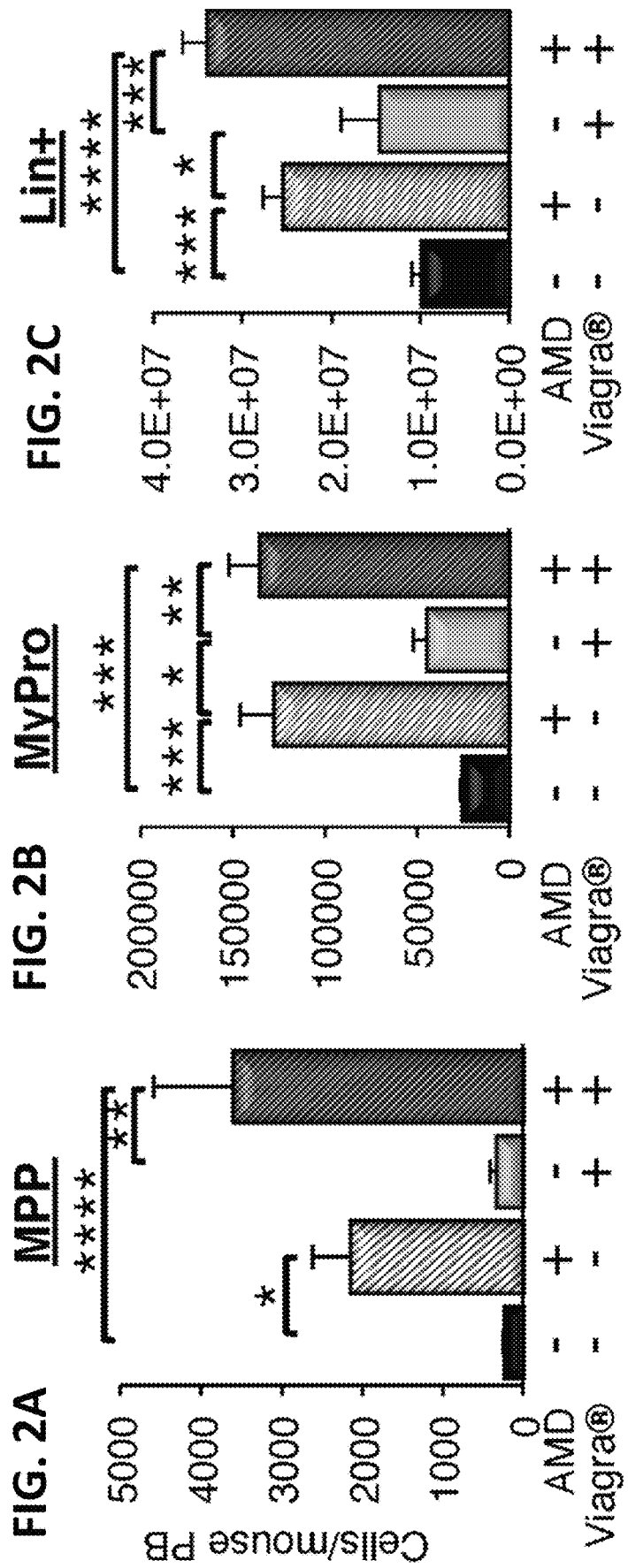

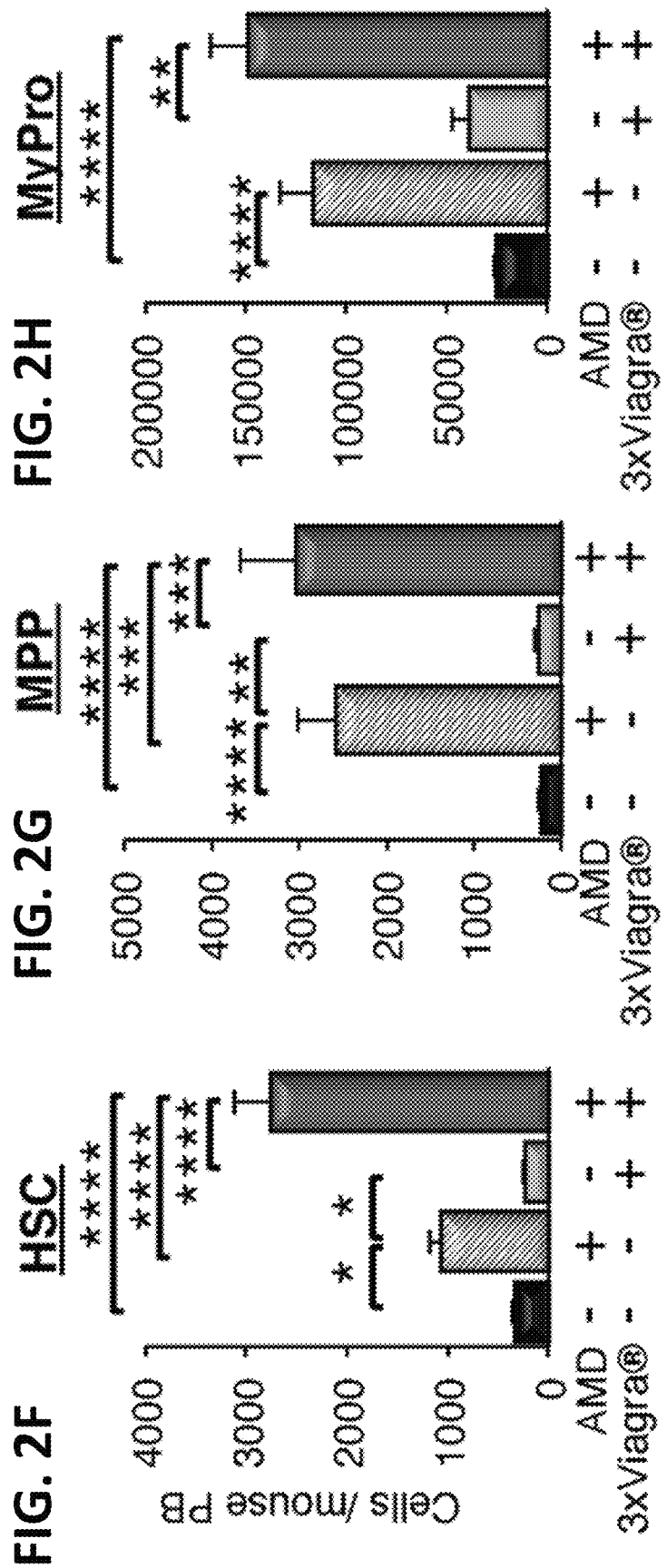

METHODS AND COMPOSITIONS FOR HEMATOPOIETIC STEM CELL MOBILIZATION

CROSS-REFERENCE TO RELATED APPLICATIONS

This application claims priority to U.S. Provisional Application No. 62/912,551, filed Oct. 8, 2019, the disclosure of which is hereby incorporated by reference in its entirety for all purposes.

BACKGROUND

Hematopoietic stem cells (HSCs) and hematopoietic progenitor cells (HPCs) have the capacity for life-long cures of a variety of disorders, but significant hurdles have caused hematopoietic cell therapies (HCTs) to be reserved mainly for patients with malignant disease that have run out of other treatment options. One such hurdle is a limited supply of donor HSCs and HPCs for transplantation and efficient methods to obtain them (Giralt et al., 2014; Korbling and Freireich, 2011). Originally, HSC-containing samples were harvested by extraction from the bone marrow (BM), but development of efficient and well-tolerated strategies for mobilizing HSCs and HPCs to the blood stream has established mobilized blood as the most common source of cells for hematopoietic transplantation. Although less invasive than BM extraction, the current standard of harvesting hematopoietic stem and progenitor cells (HSPCs) from the blood of donors treated with granulocyte-colony stimulating factor (G-CSF) for several days is complex, costly, unsuccessful in a significant proportion of donors due to prior chemotherapy, population variability, and unknown factors, and too frequently results in morbidities such as fatigue, nausea, and bone pain (Murata et al., 1999; Navarro et al., 2013; To et al., 2011).

SUMMARY

In one aspect, the disclosure features a method for hematopoietic stem cell (HSC) and/or hematopoietic progenitor cell (HPC) mobilization, comprising administering to a donor subject sildenafil citrate and AMD3100, and at least 1 hour (e.g., at least 2, 3, 4, 5, 6, 7, 8, 9, or 10 hours) after the administering, collecting the HSCs and/or HPCs from the subject. As known in the art, sildenafil citrate is marketed under the brand name Viagra®.

In some embodiments, the sildenafil citrate and AMD3100 are administered substantially simultaneously (i.e., together in the same pharmaceutical composition, or immediately after each other in two separate pharmaceutical compositions).

In some embodiments, the sildenafil citrate and AMD3100 are administered separately. For example, sildenafil citrate is administered first, followed by administering of AMD3100. In some embodiments, AMD3100 is administered at least 30 (e.g., 30, 40, 50, 60, 70, 80, 90, 100, 110, or 120) minutes after sildenafil citrate. In some embodiments, AMD3100 is administered at least 1 hour (e.g., 1, 2, 3, 4, or 5 hours) after sildenafil citrate. In some embodiments, AMD3100 is administered first, followed by administering of sildenafil citrate. In some embodiments, sildenafil citrate is administered at least 30 (e.g., 30, 40, 50, 60, 70, 80, 90, 100, 110, or 120) minutes after AMD3100. In some embodiments, sildenafil citrate is administered at least 1 hour (e.g., 1, 2, 3, 4, or 5 hours) after AMD3100.

In some embodiments, the collecting is at least 28, at least 32, at least 36, at least 40, at least 44, or at least 48 hours after the administering of both sildenafil citrate and AMD3100.

In some embodiments of this aspect, the method further comprises administering the collected HSCs and/or HPCs to a receiving subject. In some embodiments, the receiving subject has or had been treated with chemotherapy. In other embodiments, the receiving subject does not tolerate the mobilizing agent granulocyte-colony stimulating factor (GCSF). In some embodiments, the donor subject and the receiving subject are the same subject (i.e., the collected HSCs and/or HPCs are used in autologous transplantation). In other embodiments, the donor subject and the receiving subject are different subjects (i.e., the collected HSCs and/or HPCs are used in heterologous transplantation).

In another aspect, the disclosure provides a method for treating cancer, comprising administering to a subject in need thereof a population of HSCs and/or HPCs, wherein the population of HSCs and/or HPCs is collected by a method described above.

In some embodiments, the cancer is a hematopoietic disorder, such as sickle cell disease, acute promyeloid leukemia (APML), acute myelogenous leukemia (AML), chronic myelogenous leukemia (CML), acute lymphoblastic leukemia (ALL), chronic lymphocytic leukemia (CLL), prolymphocytic leukemia (PLL), hairy cell leukemia (HLL), Waldenstrom's macroglobulinemia (WM), Hodgkin's disease, Non-Hodgkin's lymphoma, peripheral T cell lymphomas, adult T cell leukemia/lymphoma (ATL), cutaneous T-cell lymphoma (CTCL), large granular lymphocytic leukemia (LGF), or Reed-Sternberg disease.

BRIEF DESCRIPTION OF THE DRAWINGS

FIGS. 1A-1J: Sildenafil citrate (Viagra') combined with AMD3100 rapidly and efficiently mobilizes functional HSCs.

FIG. 1A: Experimental design for 2-hour HSC mobilization with sildenafil citrate plus AMD3100 (top), or 5-day GCSF treatment (bottom). GCSF was administered to mice once daily for 4 days (250 µg/kg). Sildenafil citrate was administered via oral gavage (OG; 3 mg/kg) once, 1 hr prior to a single subcutaneous (SQ) injection of AMD3100 (2.5 mg/kg). Blood was collected by perfusion 1 hr after AMD3100 or 24 hrs after GCSF and analyzed by flow cytometry and multilineage reconstitution of lethally irradiated recipients.

FIG. 1B: One oral dose of sildenafil citrate significantly improves AMD3100-mediated HSC mobilization compared to AMD3100 alone. Five-day, multi-dose GCSF mobilization was not significantly better than the 2-hr sildenafil citrate+AMD3100 mobilization protocol. N=7-27 mice per cohort in 5 independent experiments. One-way ANOVA; p=0.0005. Tukey multi-parameter test; NS=not significant, p<0.001, *p<0.0005, and ****p<0.0001.

FIG. 1C: Representative flow cytometry plots of mobilized blood from FIG. 1B.

FIG. 1D: Vascular permeability increases after sildenafil citrate plus AMD3100 treatment in both the bone marrow and small intestine. Treatment schedule as in FIG. 1A, with vascular permeability tested 1 hr post-AMD3100 injection by Miles assay. Data represent three independent experiments. N=6-12 mice per cohort. One-way ANOVA; p=0.0036. Tukey multi-parameter test; *p<0.05, p<0.001, and **p<0.0001.

FIG. 1E: Donor chimerism over 5 months in lethally irradiated mice transplanted with blood from mice mobilized with AMD3100 alone or with both sildenafil citrate and AMD3100 as in the schedule shown in FIG. 1A. UBC-GFP mice were used as the mobilized donor mice, enabling identification of donor derived (GFP+) cells versus the unlabeled cells of the wild-type recipients. N=5-7 mice per cohort in 3 independent experiments. Paired t-test; *$p<0.05$ and **$p<0.01$.

FIG. 1F: Representative flow cytometry plots of UBC-GFP donor chimerism in the peripheral blood for B, T and GM cells, platelets and erythrocytes 20 weeks post-transplantation into lethally irradiated recipients from FIG. 1E.

FIG. 1G: Quantification of leukocyte lineage distribution from donor-derived cells 20 weeks post-transplantation in the mice from FIGS. 1E and 1F.

FIG. 1H: Blood from sildenafil citrate+AMD3100 mobilized mice reconstitute HSCs in the bone marrow of recipient mice. Paired t-test; *$p<0.05$.

FIGS. 1I and 1J: Long-term multilineage engraftment upon serial transplantation of bone marrow cells from the primary recipients in FIGS. 1E-1H into secondary, lethally irradiated wt hosts. Total donor chimerism in the peripheral blood over the course of the experiment is shown on the left. Quantification of donor-derived B, T and GM cells, platelets and erythrocytes 20 weeks post-transplantation is shown on the right. Data represent three independent experiments, N=9-12 mice per cohort. Unpaired t-test; *$p<0.05$, $p<0.01$, *$p<0.001$.

FIGS. 2A-2P: A variety of sildenafil citrate (Viagra®) doses and treatment schedules improve AMD3100-mediated HSC mobilization.

FIGS. 2A-2C: Mobilization of multipotent progenitors (MPP; ckit+Lin−Sca1+Flk2+CD27+ cells) and total myeloid progenitors (MyPro; ckit+Lin−Sca1-cells) in response to sildenafil citrate, AMD3100, or both, as indicated in the 2-hour protocol in FIG. 1A. N=7-27 mice per cohort in 5 independent experiments. One-way ANOVA; $p<0.0001$. Tukey multi-parameter test; *$p<0.05$, $p<0.001$, *$p<0.0005$, and ****$p<0.0001$.

FIGS. 2F-2H: Mobilization of HSCs, MPPs, and MyPros in response to the 3-day sildenafil citrate/AMD3100 indicated in FIG. 2H. N=11-27 mice per cohort in 7 independent experiments. One-way ANOVA HSC=$p<0.0001$, MPP=$p<0.0001$, MyPro=$p<0.005$. Tukey multi-parameter test; *$p<0.05$, $p<0.001$, *$p<0.0005$, and ****$p<0.0001$.

FIG. 2P: Quantification of HSCs in the blood of mice mobilized with AMD3100 and/or GCSF. Mice were mobilized with 5 mg/kg AMD3100 for 1 hour and or given once-daily SQ injections of GCSF at 250 µg/kg for 4 days. Blood was harvested and analyzed by flow cytometry on day 5. n=3 mice per cohort. One-way ANOVA; $p=0.0021$. Tukey multi-parameter test; *$p<0.05$ and **$p<0.01$.

DETAILED DESCRIPTION OF THE EMBODIMENTS

I. Introduction

Figure 1C:
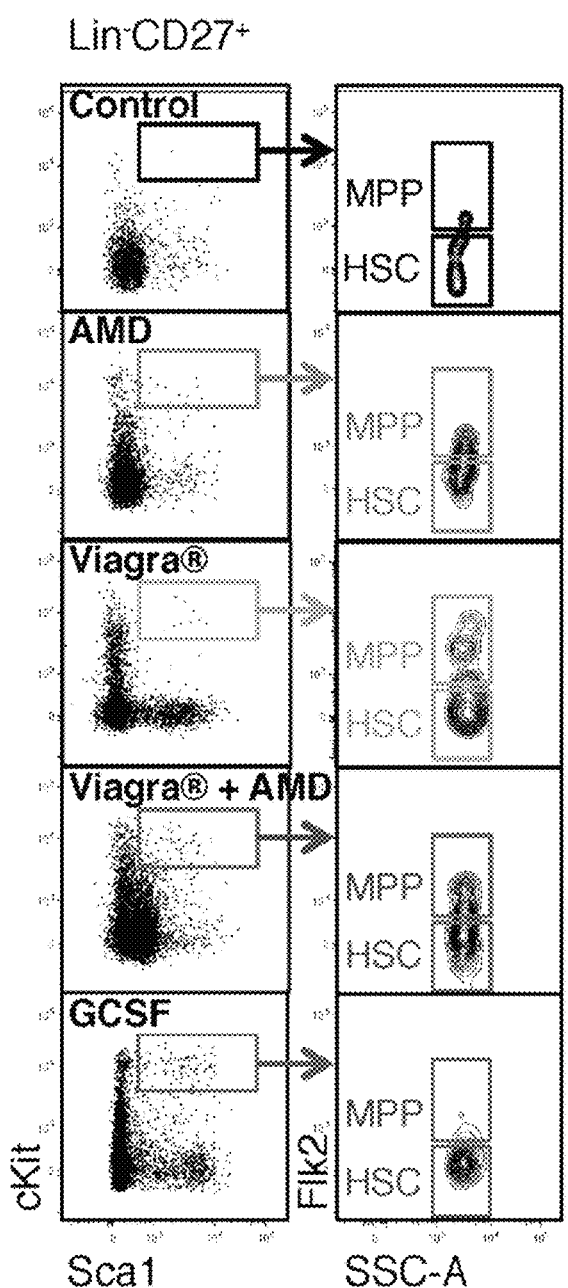

The CXCR4 antagonist AMD3100 rapidly and reproducibly mobilizes HSCs and HPCs (Broxmeyer et al., 2005; Couban et al., 2019; Devine et al., 2008), but because of its relative inefficiency as a single agent HSC mobilizer it is more commonly used as a salvaging agent when the standard G-CSF regimen fails (Douglas et al., 2018; Giralt et al., 2014). Improved harvesting protocols would significantly improve the success rate for current indications and open curative HCT to a wider spectrum of disorders. New mobilization regimens can also reveal mechanisms of HSC retention in the BM.

Despite the use of HSCs and HPCs in clinical therapy for over half a century and the urgent need for improved strategies, the mechanisms regulating HSC and HPC trafficking remain unclear. We recently reported that the transmembrane receptor ROBO4 regulates directional trafficking of HSCs and HPCs across the vascular endothelium to and from the BM (Smith-Berdan et al., 2011, 2015). Deletion of ROBO4 results in increased vascular permeability (Jones et al., 2008; Smith-Berdan et al., 2015) and increased numbers of HSCs and HPCs in the blood stream (Smith-Berdan et al., 2015). Upon testing the effects of induced vascular permeability on HSC trafficking, we reported increased vascular leakage as well as 2-3-fold increases in HSC numbers in the blood within 15 minutes of an intravenous administration of rhVEGF164 or histamine (Smith-Berdan et al., 2015). This revealed that induced vascular permeability, by itself, is sufficient to mobilize HSCs and HPCs.

Additionally, we showed that VEGF-induced vascular permeability significantly improved AMD3100-mediated mobilization of engraftable HSCs and HPCs (Smith-Berdan et al., 2015). Subsequently, Pelus and colleagues reported similar findings using Neuropeptide Y (Singh et al., 2017) and GROβ, a CXCR2 agonist that induces vascular permeability (Hoggatt et al., 2018).

As pharmacokinetics and allelic variations in CXCR2 preclude effective or universal use of VEGF (Giacca and Zacchigna, 2012) and GROβ (Hoggatt et al., 2018) in humans, we investigated whether currently FDA-approved vasomodulators can be repurposed for HSC mobilization. Here, we tested the effects of sildenafil citrate (Viagre), a phosphodiesterase type 5 (PDE5) inhibitor, on HSC mobilization. PDE5 inhibitors block degradation of cyclic GMP in the smooth muscle cells lining blood vessels, resulting in vasodilation. This inhibition is immediate, with a peak activity 2 hours post-oral administration of the drug (Andersson, 2018). Sildenafil citrate was originally developed to combat high blood pressure, coronary heart disease and angina pectoris and is currently successfully used to treat a variety of vascular disorders, including pulmonary hypertension, altitude sickness, Raynaud's Syndrome, preeclampsia and erectile dysfunction (Andersson, 2018). Here, we reveal that sildenafil citrate should also be considered in combination therapy for very rapid and efficient, single-day HSC and HPC mobilization.

The disclosure provides methods for hematopoietic stem cell (HSC) and/or hematopoietic progenitor cell (HPC) mobilization that include administering to a donor subject sildenafil citrate and AMD3100, and at least 1 hour after the administering, collecting the HSCs and HPCs from the subject.

II. Methods of Mobilization

The disclosure provides a method for hematopoietic stem cell (HSC) and/or hematopoietic progenitor cell (HPC) mobilization, comprising administering to a donor subject sildenafil citrate and AMD3100, and at least 1 hour after the administering, collecting the HSCs and/or HPCs from the subject.

In some embodiments of the methods for HSCs and/or HPCs mobilization described herein, sildenafil citrate and AMD3100 can be administered substantially simultaneously, i.e., administered together in a single pharmaceutical composition or administered sequentially in separate pharmaceutical compositions. When sildenafil citrate and AMD3100 are administered in separate pharmaceutical compositions, in some embodiments, the two pharmaceutical compositions are administered sequentially, i.e., within less than 5 minutes of each other (e.g., administered within 1, 2, 3, 4, or 5 minutes of each other).

When sildenafil citrate and AMD3100 are administered in separate pharmaceutical compositions, in other embodiments, the two pharmaceutical compositions are administered chronologically apart, i.e., more than 5 minutes of each other (e.g., administered at least 6, 10, 15, 20, 30, 40, 50, 60, 70, 80, 90, 100, 110, or 120 minutes apart). In some embodiments, sildenafil citrate is administered first, followed by AMD3100 administered at least 30 (e.g., 30, 40, 50, 60, 70, 80, 90, 100, 110, or 120) minutes afterwards. In some embodiments, AMD3100 is administered first, followed by sildenafil citrate administered at least 30 (e.g., 30, 40, 50, 60, 70, 80, 90, 100, 110, or 120) minutes afterwards. In some embodiments, sildenafil citrate is administered orally and AMD3100 is administered via injection, e.g., intravenous injection.

After sildenafil citrate and AMD3100 are administered, the HSCs and/or HPCs can be collected at least 1 hour (e.g., at least 2, 3, 4, 5, 6, 7, 8, 9, or 10 hours) after the administering of both sildenafil citrate and AMD3100.

The method can further comprise administering the collected HSCs and/or HPCs to a receiving subject (e.g., a receiving subject who has or had been treated with chemotherapy; a receiving subject who does not tolerate the mobilizing agent granulocyte-colony stimulating factor (GCSF). In some embodiments, the donor subject and the receiving subject are the same subject (i.e., the collected HSCs and/or HPCs are used in autologous transplantation). In other embodiments, the donor subject and the receiving subject are different subjects (i.e., the collected HSCs and/or HPCs are used in heterologous transplantation).

The collected HSCs and/or HPCs can be used to treat cancer, which can be a hematopoietic disorder. Examples of hematopoietic disorders include, but are not limited to, acute promyeloid leukemia (APML), acute myelogenous leukemia (AML), chronic myelogenous leukemia (CML), acute lymphoblastic leukemia (ALL), chronic lymphocytic leukemia (CLL), prolymphocytic leukemia (PLL), hairy cell leukemia (HLL), Waldenstrom's macroglobulinemia (WM), Hodgkin's disease, Non-Hodgkin's lymphoma, peripheral T cell lymphomas, adult T cell leukemia/lymphoma (ATL), cutaneous T-cell lymphoma (CTCL), large granular lymphocytic leukemia (LGF), and Reed-Sternberg disease.

III. Methods of Treatment

The disclosure includes methods for the treatment of subjects who are in need of increased numbers of HSCs and/or HPCs. In some embodiments, the subject is scheduled to or intends to donate stem cells, e.g., for use in heterologous or autologous transplantation. Generally, the methods include mobilizing the HSCs and/or HPCs by administering to a donor subject sildenafil citrate and AMD3100, collecting the HSCs and/or HPCs at least 1 hour (e.g., at least 2, 3, 4, 5, 6, 7, 8, 9 or 10 hours) after the administration, and further administering a therapeutically effective amount of the collected HSCs and/or HPCs to a receiving subject who is in need of such treatment. In some embodiments, the receiving subject has or had been treated with chemotherapy. In other embodiments, the receiving subject does not tolerate the mobilizing agent granulocyte-colony stimulating factor (GCSF). In certain embodiments, the receiving subject has sickle cell disease (e.g., Hemoglobin S130 thalassemia, Hemoglobin Sβ+ thalassemia, Hemoglobin SC, Hemoglobin SD, Hemoglobin SE, or Hemoglobin SS). In certain embodiments, the donor subject and the receiving subject are the same person (e.g., autologous transplantation). In other embodiments, the donor subject and the receiving subject are different persons (e.g., heterologous transplantation).

Administration of the collected HSCs and/or HPCs for treatment will result in an increased number of HSCs and/or HPCs. In some embodiments, such administration will result in an increase of about 10- to 500-fold (e.g., 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 410-fold, 420-fold, 430-fold, 440-fold, 450-fold, 460-fold, 470-fold, 480-fold, 490-fold, or 500-fold) in the number of HSCs and/or HPCs in the receiving subject. Methods of measuring such increases are known in the art, see, e.g., Neben et al., *Blood.* 1993; 81(7):1960-7; Ashihara et al. Exp. Hematol. 2000; 28(3):311-7; Pruijt et al., *Proc. Nail. Acad. Sci. U.S.A.* 1999; 96(19):10863-8).

An effective amount of the collected HSCs and/or HPCs can be administered in one or more administrations, applications, or dosages. The collected HSCs and/or HPCs can be administered one from one or more times per day to one or more times per week; including once every other day. The skilled artisan will appreciate that certain factors may influence the dosage and timing required to effectively treat a subject, including but not limited to previous treatments, the general health and/or age of the subject, and other diseases present. Moreover, treatment of a subject with the collected HSCs and/or HPCs described herein can include a single treatment or a series of treatments.

Subjects that can be treated using the collected HSCs and/or HPCs include, e.g., subjects who have cancers, especially blood cancers. For example, the collected HSCs and/or HPCs can be transplanted into subjects who have cancers that are resistant to treatment with radiation therapy or chemotherapy, e.g., to restore stem cells that were destroyed by high doses of chemotherapy and/or radiation therapy used to treat the cancers. In other embodiments, subject can be treated using the collected HSCs and/or HPCs also include, e.g., subjects who have non-hematopoietic disorders such as metabolic or neurological disorders.

In some embodiments, the subject has a hematopoietic neoplastic disorder. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. In some embodiments, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to Hodgkin's Disease and Medium/High grade (aggressive) Non-Hodgkin's lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. In some embodiments, the methods of treatment can include administering the collected HSCs and/or HPCs to restore stem cells that were destroyed by high doses of chemotherapy and/or radiation therapy, e.g., therapy used to treat the disorders. In other embodiments, the subject who is treated has a non-malignant disorder such as aplastic anemia, a hemoglobinopathy, including sickle cell anemia, or an immune deficiency disorder. In other embodiments, the subject who is treated has sickle cell disease (e.g., Hemoglobin Sβ0 thalassemia, Hemoglobin Sβ+ thalassemia, Hemoglobin SC, Hemoglobin SD, Hemoglobin SE, or Hemoglobin SS).

IV. Mobilization

The value of alternative HSC and/or HPC mobilization regimens to complement GCSF-based protocols is multiple. GCSF, and GCSF plus AMD3100 (FIGS. 2P and 2Q), effectively mobilizes HSCs and/or HPCs in the majority of donors and will likely persist as a common clinical procedure. Importantly, however, a mobilization regimen that does not involve cell expansion, yet offers robust yields of HSCs and/or HPCs, would increase the availability of HCT for autologous candidates that cannot tolerate the standard GCSF mobilization treatment, such as the very ill, elderly, or sickle-cell patients (Fitzhugh et al., 2009; Giralt et al., 2014).

New mobilization strategies are also needed to reduce the incidence of mobilization failure, which continues to hamper HCT success, especially for patients with a history of chemotherapy (Demirer et al., 1996; Gertz, 2010; Morgan et al., 2004; To et al., 2011). Sildenafil citrate and other rapidly acting HSC mobilizers such as VEGFR agonists, Neuropeptide Y, the CXCR2 agonist GROβ, and the integrin inhibitors Bio5192a and BOP (Cao et al., 2016; Hoggatt et al., 2018; Ramirez et al., 2009; Singh et al., 2017; Smith-Berdan et al., 2015) are promising candidates for overcoming these challenges. Novel regimens may also reduce side-effects, including the bone pain and nausea that frequently accompanies GCSF treatment (Murata et al., 1999; Navarro et al., 2013; To et al., 2011). Importantly, sildenafil citrate alone did not lead to detectable increases in HSPCs in the blood, eliminating concerns of inadvertent HSC mobilization in patients using sildenafil citrate for other indications.

Cost reduction is another consideration. Viagra® generics, at ~$2 per human dose equivalent to 3 mg/kg, is cheaper than GCSF/Neupogen/Filgrastim which costs 3,800 per treatment regimen (BC Cancer, 2018; Consumer Reports, 2019; Shaughnessy et al., 2011; James et al., 2017). Additional cost reductions are also afforded by the simplicity of oral intake of sildenafil citrate versus the multi-day injections required for GCSF. The combined benefits of reduced time commitment and complexity of administration, and the more beneficial side-effect profile of sildenafil citrate versus GCSF, would likely attract more volunteer donors and make HCT a reality for additional patient cohorts.

Lastly, this study solidifies vascular integrity as an essential regulator of HSC trafficking (Smith-Berdan et al., 2015; Singh et al., 2017; Hoggatt et al., 2018). The discovery of vasomodulating drugs as HSC mobilizers provides new mechanistic insights into the regulation of HSC location and inspires additional investigations to control cellular trafficking.

V. Pharmaceutical Compositions

In some embodiments of the methods for HSCs and/or HPCs mobilization described herein, sildenafil citrate and AMD3100 can be administered in a single pharmaceutical composition. In other embodiments, sildenafil citrate and AMD3100 can be administered in separate pharmaceutical compositions.

The pharmaceutical compositions can contain one or more pharmaceutically acceptable carriers or excipients, which can be formulated by methods known to those skilled in the art. Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. Pharmaceutical compositions of the invention can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium).

Pharmaceutical compositions including sildenafil citrate and/or AMD3100 encompass any pharmaceutically acceptable salts or esters thereof, which, upon administration to a mammal (e.g., a human), is capable of providing (directly or indirectly) the biologically active form. For example, a pharmaceutically acceptable salt of sildenafil citrate can be sildenafil citrate. Accordingly, for example, the disclosure is also drawn to pharmaceutically acceptable salts of prodrugs, pharmaceutically acceptable salts of such prodrugs, and other bioequivalents. Suitable pharmaceutically acceptable salts include, but are not limited to, citrate, sodium, and potassium salts.

In some embodiments, other acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. In some embodiments, carriers and excipients are selected from water, salt solutions, alcohol, polyethylene glycols, gelatin, lactose, amylase, magnesium stearate, talc, silicic acid, viscous paraffin, hydroxymethylcellulosem, and polyvinylpyrrolidone.

EXAMPLES

Example 1

Experimental Procedures

Mouse lines. All animals were housed and bred in the AALAC accredited vivarium at UC Santa Cruz. C57BL6 (JAX Cat #000664), B6 CD45.1 BoyJ (JAX Cat #002014), and UBC-GFP (JAX Cat #004353) mice were maintained according to approved protocols by UCSC's Institutional Animal Care and Use Committee (IACUC). Adult mice were used between 8-16 weeks of age and randomized based on sex.

Mobilization/tissue isolation. Mice were treated with subcutaneous (SQ) injections of rhGCSF (Amgen, Thousand Oaks, CA, 250 µg/kg) or a single dose of AMD3100 (Sigma, 2.5 mg/kg or 5 mg/kg where specified), or by oral gavage (OG) with sildenafil citrate (Viagra®; Sigma; 3, 10 or 30 mg/kg) (Motta et al., 2015) as indicated. Maximum blood was obtained by perfusing the mouse with PBS/20 mM EDTA through the left ventricle, clipping the right atrium and collecting the pooled perfused blood in the chest cavity. The total blood was processed for cell counts and flow cytometry analysis, as described previously (Smith-Berdan et al., 2011, 2015). Briefly, cells were pelleted by centrifugation, washed with 2% donor calf serum in PBS to remove EDTA, then incubated with fluorescently conjugated antibodies for flow cytometry analysis or resuspended in HBSS for transplantation into conditioned recipients.

Transplantation of mobilized HSPCs. Reconstitution assays were performed by transplanting half of the total cells obtained by perfusion per mouse into sub-lethally irradiated hosts (742 rads) and a third of the total cells obtained by perfusion per mouse into lethally irradiated hosts (1025 rads). Donor mice were either C57BL6 or UBC-GFP, transplanted into congenic B6 CD45.1 BoyJ or C57BL6 irradiated hosts (Boyer et al., 2019; Smith-Berdan et al., 2015). Recipient mice were bled at the indicated intervals post-transplantation via the tail vein for peripheral blood analysis, and BM cells were harvested >16 wks post-transplantation.

Flow cytometry. Cell labeling was performed on ice in 1× PBS with 5 mM EDTA and 2% serum. Antibodies used are listed in the supplemental table. Samples were analyzed for donor chimerism (detectable by either GFP or antibodies targeted at the CD45.1/2 locus) on an LSRII or AriaIII (Becton Dickinson, San Jose, CA), as described previously (Beaudin et al., 2016; Boyer et al., 2011, 2019; Leung et al., 2019; Smith-Berdan et al., 2011, 2015; Ugarte et al., 2015).

Vascular permeability. A modified Miles Assay was utilized to assess in vivo vascular permeability (Miles and Miles, 1952; Smith-Berdan et al., 2015). Post-treatment with AMD3100 and/or sildenafil citrate, mice were injected IV with Evans Blue (50 mg/kg). Dye was allowed to leak into tissues for 10 minutes prior to euthanization by isoflurane inhalation. Vascular leak was measured as OD650/tissue mass after Evans Blue extraction from tissues by incubation in formamide for 3-5 hours at 55° C.

Quantification and statistical analysis. Number of experiments, N, and what N represents can be found in the legend for each figure. Statistical significance was determined by two-tailed unpaired student's T-test or one-way ANOVA followed by Tukey's multiple comparisons test. All data are shown as mean±standard error of the mean (SEM) representing at least three independent experiments.

Example 2

Effects of Sildenafil Citrate and AMD3100

Figure 2D:
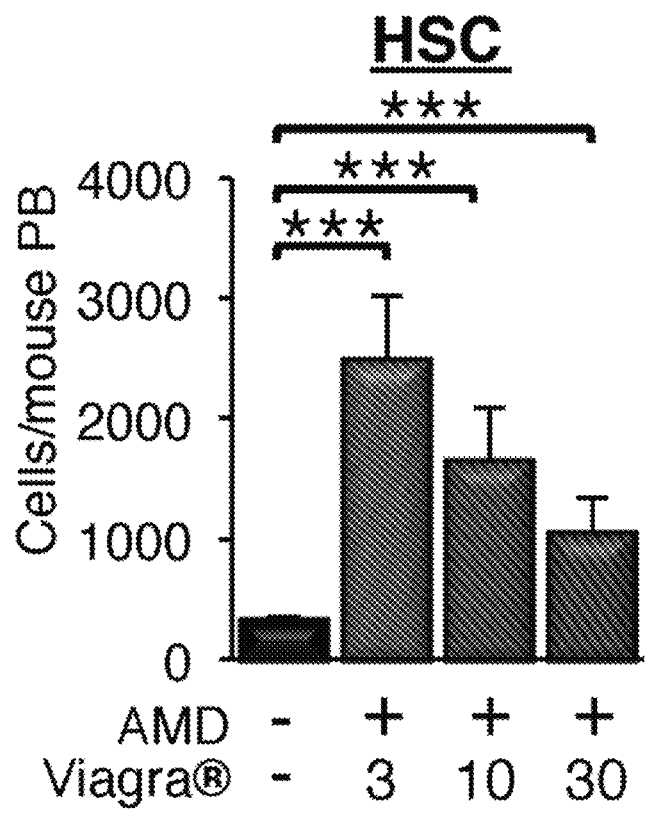
FIG. 2D: Sildenafil citrate dose titration. Increasing the amount of sildenafil citrate from 3 to 10 or 30 mg/kg does not further improve sildenafil citrate enhancement of AMD3100-mediated HSC mobilization. Drugs were administered as in the 2-hour protocol of FIG. 1A. N=4-27 mice per cohort in 2-5 independent experiments. One-way ANOVA; $p<0.0001$. Tukey multi-parameter test; *$p<0.05$, $p<0.001$, *$p<0.0005$, and **** $p<0.0001$.
Figure 2E:
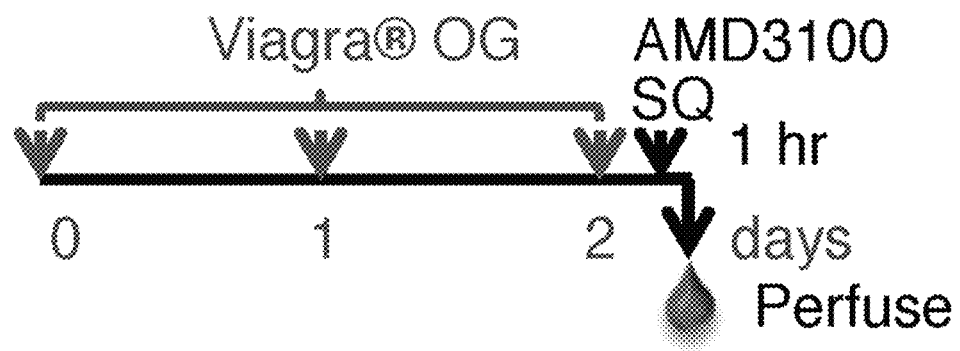
FIG. 2E: Experimental design for HSC mobilization with multiple daily doses of sildenafil citrate. Sildenafil citrate was administered orally (OG) at 10 mg/kg once daily for 3 days. AMD3100 (2.5 mg/kg-5 mg/kg) was injected subcutaneously (SQ) 1 hour after the third sildenafil citrate dose, followed 1 hour later by blood perfusion and analysis.

To test whether sildenafil citrate (Viagre), like injections of histamine or VEGF (Smith-Berdan et al., 2015), was capable of mobilizing HSCs, we first administered a single dose of sildenafil citrate via oral gavage at 3 mg/kg (Mona et al., 2015; US FDA, 2018) (FIG. 1A). Analysis of total perfused blood 2 hrs post sildenafil citrate treatment did not lead to detectable increases in HSCs (defined as cKIT+ lineage-SCA1+CD27+FLK2-cells; FIGS. 1B and 1C) or other hematopoietic cells (FIGS. 2A-2C). Similarly, higher doses of sildenafil citrate (10 mg/kg) administered as in FIG. 1A or for 3 consecutive days failed to mobilize significant numbers of HSCs (FIGS. 2D-2F).

In contrast, a single subcutaneous dose of the CXCR4 antagonist AMD3100, a known inducer of HSC mobilization (Broxmeyer et al., 2005), led to modest, but reproducible, HSC mobilization (FIGS. 1B and 1C; FIGS. 2A-2C).

Figure 2I:
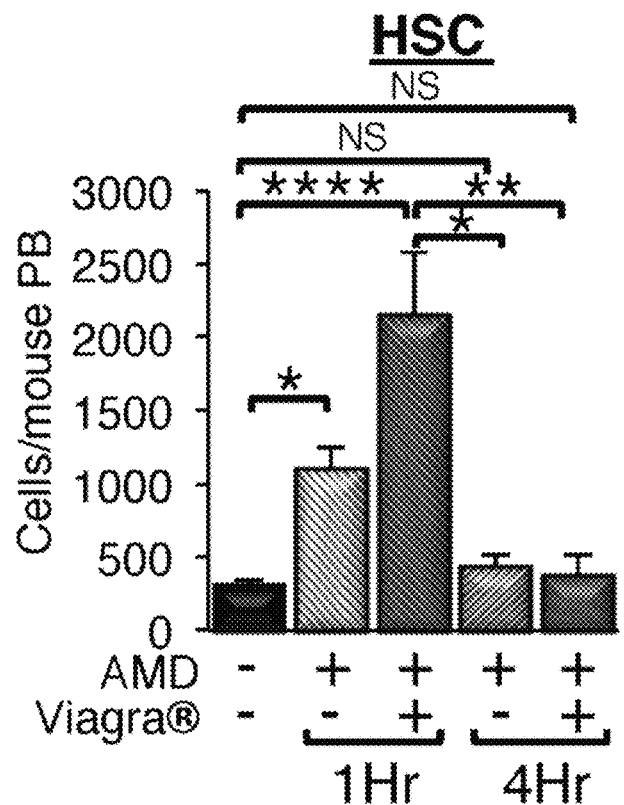
FIG. 2I: The number of HSCs in the blood return to steady-state levels 4 hours post-treatment with AMD3100 alone or both sildenafil citrate and AMD3100. Mice were injected with sildenafil citrate and AMD3100 per the schedule described in FIG. 1A, except perfusion and blood analysis were performed 4 hours post AMD3100. N=6-22 mice per cohort in 3 independent experiments. One-way ANOVA; $p<0.0001$. Tukey multi-parameter test; *$p<0.05$, $p<0.001$, *$p<0.0005$, and ****$p<0.0001$.

We next tested the effects of sildenafil citrate combined with AMD3100. Remarkably, a single oral dose of sildenafil citrate significantly improved AMD3100-induced HSC mobilization in a rapid, 2-hour protocol (FIGS. 1A-1C). The mobilization was transient, as the numbers of HSCs in the blood had returned to normal 4 hrs post-treatment (FIG. 2I).

The HSC mobilization efficiency with 2-hour sildenafil citrate plus AMD3100 was comparable to that of a 5-day GCSF protocol (250 μg/kg daily subcutaneous injections) (FIGS. 1A-1C).

Higher doses of sildenafil citrate (10 and 30 mg/kg) also improved AMD3100-mediated HSC mobilization, but were not more effective than 3 mg/kg (FIG. 2D). Further, a 3-day oral sildenafil citrate regimen combined with a single AMD3100 injection led to significantly more HSCs in the bloodstream than AMD3100 alone (FIGS. 2E and 2F).

Compared to control mice, the numbers of phenotypic HSCs increased 2.9-, 7.5- and 8.4-fold with AMD3100 alone; AMD3100 plus a single sildenafil citrate dose; and AMD3100 plus 3 days of sildenafil citrate, respectively. The numbers of HSCs in the bloodstream in the rapid (~2,500 HSCs/mouse) and 3-day (~2,800 HSCs/mouse) sildenafil citrate/AMD3100 combination were similar to the numbers present 1 day after four consecutive days of G-CSF injections (~3,400 HSCs/mouse; FIG. 1B).

Example 3

Vascular Permeability

Figure 1D:
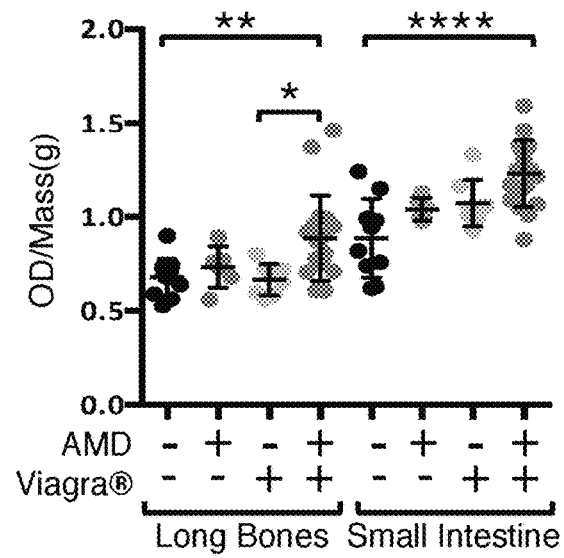
Figure 1E:
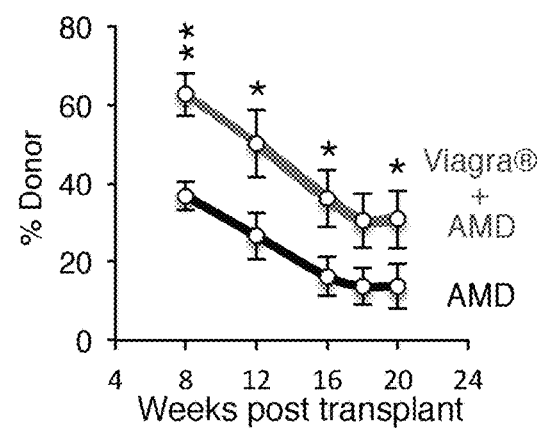
Figure 1F:
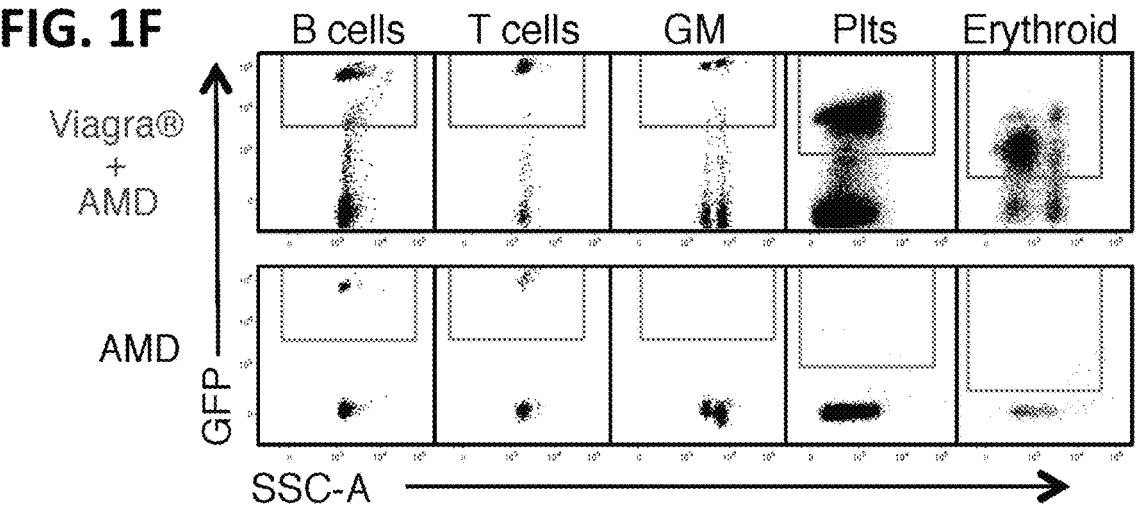
Figure 1F:
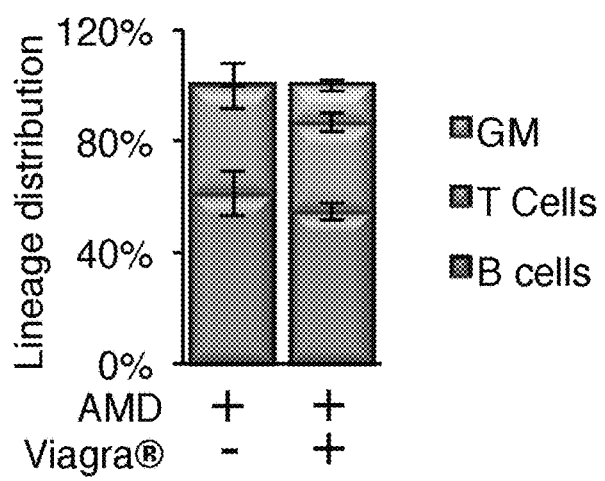
Figure 1F:
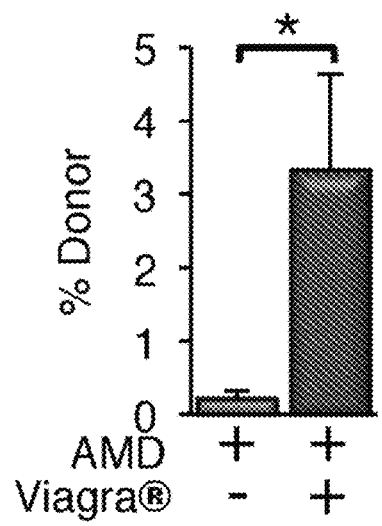
Figure 2J:
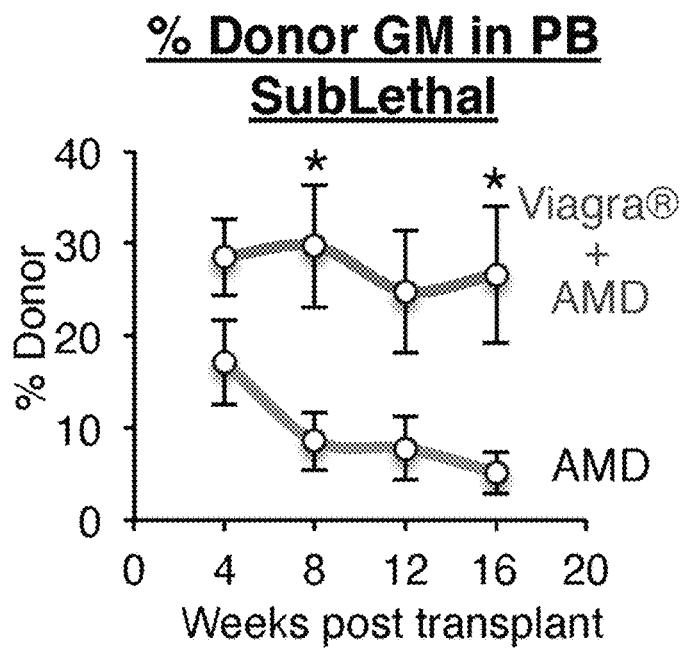
FIG. 2J: Peripheral blood donor chimerism over 4; months in sublethally irradiated (742 rad; ¾ lethal dose) mice transplanted with blood from mice mobilized with AMD3100 alone or with both sildenafil citrate and AMD3100 as in the schedule shown in FIG. 1A. UBC-GFP mice were used as the mobilized donor mice, enabling identification of donor-derived (GFP+) cells versus the unlabeled cells of the wild-type recipients. GM, granulocyte/myelomonocytic cells. N=6-9 mice per cohort in 3 independent experiments. Unpaired t-test; $p<0.05$.
Figure 2K:
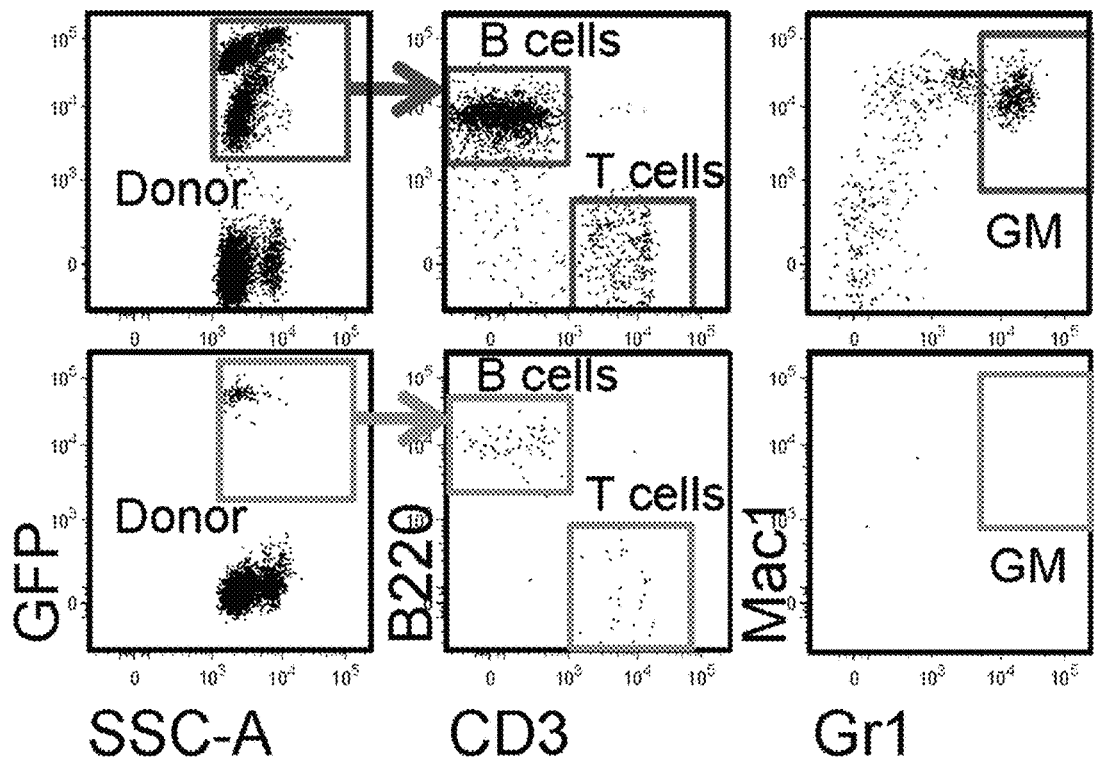
FIGS. 2K and 2L: Representative flow cytometry plots (FIG. 2K) and quantification of leukocyte lineage distribution (FIG. 2L) of donor-derived cells >16 weeks post-transplantation in the mice from FIG. 2J.
Figure 2L:
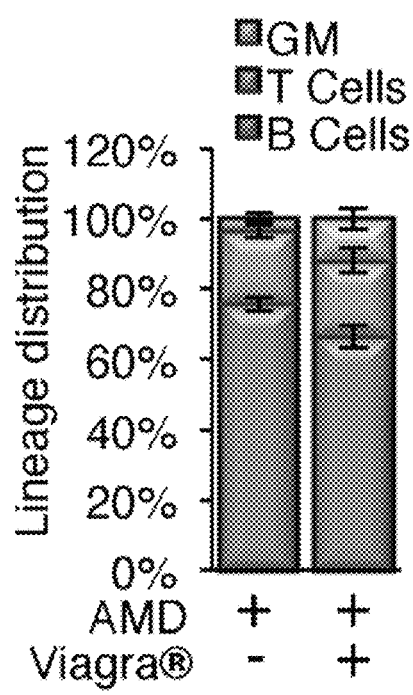

Assessment of vascular permeability by Miles assay revealed that sildenafil citrate (Viagra®) plus AMD3100 led to increased vascular leak (FIG. 1D), consistent with sildenafil citrate acting as a vasodilator, and with vascular permeability leading to HSC mobilization (Smith-Berdan et al., 2015; Singh et al., 2017; Hoggatt et al., 2018). Transplantation into lethally (FIGS. 1E-1G) and sublethally (FIGS. 2J, 2K, and 2L) conditioned recipients demonstrated that the blood from mice treated with sildenafil citrate plus AMD3100 contained an increased number of functional, long-term engrafting multipotent HSCs compared to the blood from mice treated with AMD3100 alone.

Figure 2M:
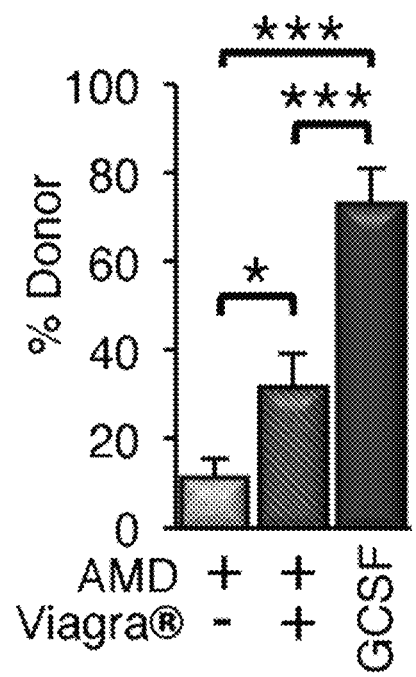
FIG. 2M: Quantification of total donor chimerism 20 weeks post-transplantation in recipients transplanted with blood from mice (FIG. 1B) mobilized with AMD3100 alone, AMD3100 plus sildenafil citrate, or GCSF, as in the treatment schedules indicated in FIG. 1A. N=4-7 mice per cohort in 3 independent experiments. ANOVA; $p<0.0001$. Tukey multi-parameter test; *$p<0.05$, ***$p<0.0005$.
Figure 2N:
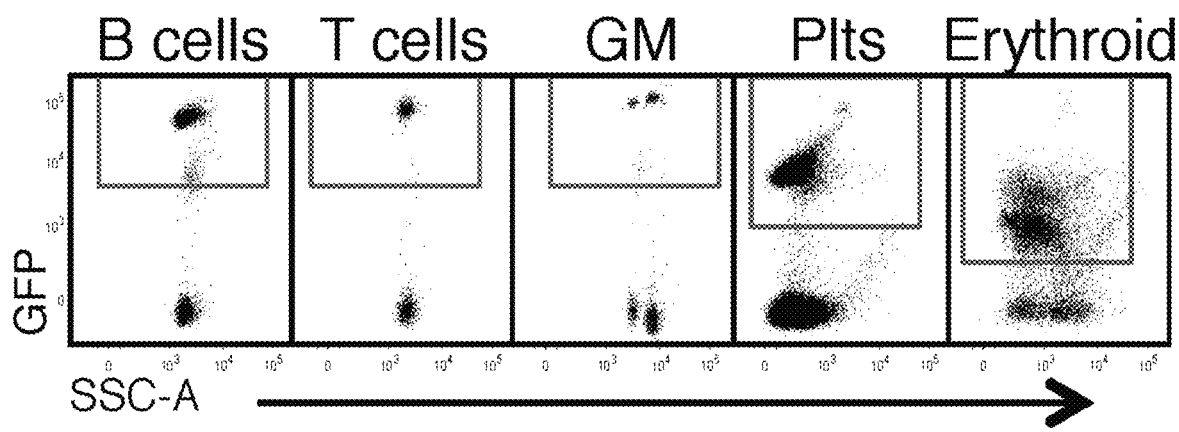
FIG. 2N: Representative flow cytometry plots of lineage chimerism in the peripheral blood of the GCSF mobilized mice from FIG. 2L >16 weeks post-transplantation.
Figure 2O:
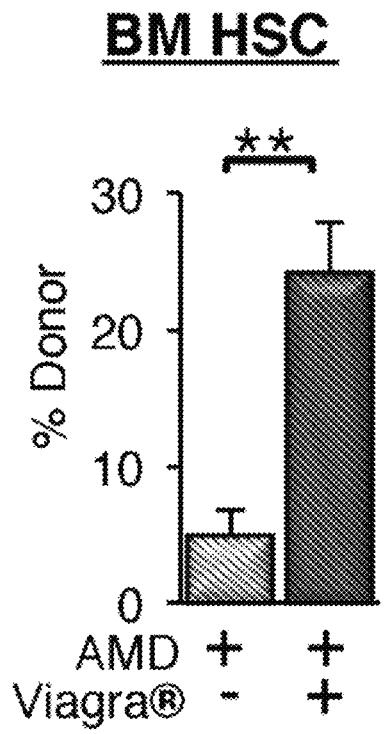
FIG. 2O: Blood from sildenafil citrate+AMD3100 mobilized mice reconstitute HSCs in the bone marrow of recipient mice. Quantification of HSC chimerism in the bone marrow of the mice from FIG. 2J >16 weeks post-transplantation. Unpaired t-test; ** $p<0.01$.
Figure 2P:
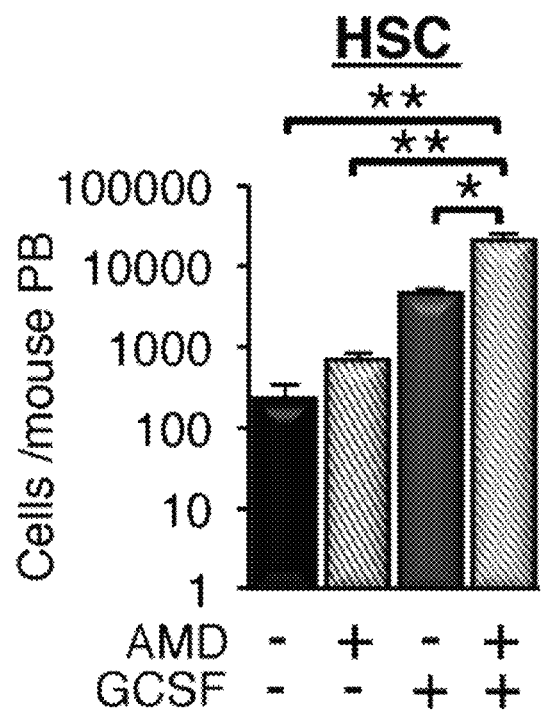
Figure 2Q:
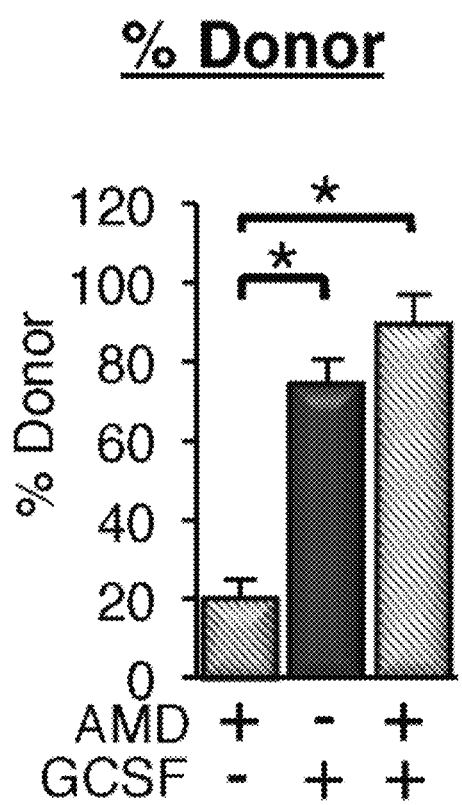
FIG. 2Q: Peripheral blood donor chimerism over 4 months in sublethally irradiated (525 rad; ½ lethal dose) mice transplanted with blood from mice mobilized with AMD3100 or GCSF alone or with both AMD3100 and GCSF (donor mice from panel K). One-way ANOVA; $p=0.0163$ Tukey multi-parameter test; *$p<0.05$.

Although GCSF did not lead to significantly higher numbers of phenotypic HSCs in the blood compared to sildenafil citrate plus AMD3100 (FIG. 1B), blood from GCSF-mobilized donors reconstituted recipients more robustly (FIGS. 2M and 2N), consistent with GCSF selectively mobilizing the most quiescent HSCs (Bernitz et al., 2017). Similarly, the BM of recipients of blood from donors treated with both sildenafil citrate and AMD3100 contained significantly more donor HSCs than the BM of recipients of blood cells from mice treated with AMD3100 alone (FIG. 1H and FIG. 2O). Transplantation of BM cells from lethally irradiated primary recipients into secondary hosts also led to long-term, multilineage engraftment, with sildenafil citrate plus AMD3100 outperforming AMD3100 alone (FIGS. 1I and 1J). Thus, the combination of sildenafil citrate and AMD3100 enables rapid and efficient mobilization of serially long-term reconstituting, self-renewing, and multipotent HSCs.

REFERENCES

Andersson, K. E. (2018). PDE5 inhibitors—pharmacology and clinical applications 20 years after sildenafil discovery. Br. J. Pharmacol. 175, 2554-2565.

BC Cancer (2018). The Leukemia/Bone Marrow Transplant Program. Accessed September 2018.

Beaudin, A. E., Boyer, S. W., Perez-Cunningham, J., Hernandez, G. E., Derderian, S. C., Jujjavarapu, C., Aaserude, E., MacKenzie, T., and Forsberg, E. C. (2016). A Transient Developmental Hematopoietic Stem Cell Gives Rise to Innate-like B and T Cells. Cell Stem Cell 19, 768-783.

Bernitz, J. M., Daniel, M. G., Fstkchyan, Y. S., and Moore, K. (2017). Granulocyte colony-stimulating factor mobilizes dormant hematopoietic stem cells without proliferation in mice. Blood 129, 1901-1912.

Boyer, S. W., Schroeder, A. V., Smith-Berdan, S., and Forsberg, E. C. (2011). All Hematopoietic Cells Develop from Hematopoietic Stem Cells through Flk2/Flt3-Positive Progenitor Cells. Cell Stem Cell 9, 64-73.

Boyer, S. W., Rajendiran, S., Beaudin, A. E., Smith-Berdan, S., Muthuswamy, P. K., Perez-Cunningham, J., Martin, E. W., Cheung, C., Tsang, H., Landon, M., et al. (2019). Clonal and Quantitative In Vivo Assessment of Hematopoietic Stem Cell Differentiation Reveals Strong Erythroid Potential of Multipotent Cells. Stem Cell Reports 12, 801-815.

Broxmeyer, H. E., Orschell, C. M., Clapp, D. W., Hangoc, G., Cooper, S., Plett, P. A., Liles, W. C., Li, X., Graham-Evans, B., Campbell, T. B., et al. (2005). Rapid mobilization of murine and human 11 hematopoietic stem and progenitor cells with AMD3100, a CXCR4 antagonist. J. Exp. Med. 201, 1307-1318.

Cao, B., Zhang, Z., Grassinger, J., Williams, B., Heazlewood, C. K., Churches, Q. I., James, S. A., Li, S., Papayannopoulou, T., and Nilsson, S. K. (2016). Therapeutic targeting and rapid mobilization of endosteal HSC using a small molecule integrin antagonist. Nat. Commun. Consumer Reports (2017). Accessed July 2019.

Couban, S., Wong, P. C., and Schultz, K. R. (2019). The case for plerixafor to replace filgrastim as the optimal agent to mobilize peripheral blood donors for allogeneic hematopoietic cell transplantation. Exp Hematol. 70, 1-9.

Demirer, T., Buckner, C. D., Gooley, T., Appelbaum, F. R., Rowley, S., Chauncey, T., Lilleby, K., Storb, R., and Bensinger, W. I. (1996). Factors influencing collection of peripheral blood stem cells in patients with multiple myeloma. Bone Marrow Transpl. 17, 937-941.

Devine, S. M., Vij, R., Rettig, M., Todt, L., McGlauchlen, K., Fisher, N., Devine, H., Link, D. C., Calandra, G., Bridger, G., et al. (2008). Rapid mobilization of functional donor hematopoietic cells without G-CSF using AMD3100, an antagonist of the CXCR4/SDF-1 interaction. Blood 112, 990-998.

Douglas, K. W., Gilleece, M., Hayden, P., Hunter, H., Johnson, P. R. E., Kallmeyer, C., Malladi, R. K., Paneesha, S., Pawson, R., Quinn, M., et al. (2018). UK consensus statement on the use of plerixafor to facilitate autologous peripheral blood stem cell collection to support high-dose chemoradiotherapy for patients with malignancy. J. Clin. Apher. 33, 46-59.

Fitzhugh, C. D., Hsieh, M. M., Bolan, C. D., Saenz, C., and Tisdale, J. F. (2009). Granulocyte colonystimulating factor (G-CSF) administration in individuals with sickle cell disease: Time for a moratorium? Cytotherapy 11, 464-471.

Gertz, M. A. (2010). Current status of stem cell mobilization. Br. J. Haematol. 150, 647-662.

Giacca, M., and Zacchigna, S. (2012). VEGF gene therapy: therapeutic angiogenesis in the clinic and beyond. Gene Ther 19, 622-629.

Giralt, S., Costa, L., Schriber, J., DiPersio, J., Maziarz, R., McCarty, J., Shaughnessy, P., Snyder, E., Bensinger, W., Copelan, E., et al. (2014). Optimizing autologous stem cell mobilization strategies to improve patient outcomes: Consensus guidelines and recommendations. Biol. Blood Marrow Transplant. 20, 295-308.

Hoggatt, J., Singh, P., Tate, T. A., Chou, B. K., Datari, S. R., Fukuda, S., Liu, L., Kharchenko, P. V., Schajnovitz, A., Baryawno, N., et al. (2018). Rapid Mobilization Reveals a Highly Engraftable Hematopoietic Stem Cell. Cell 172, 191-204.

James, E., Trautman, H., Szabo, E., and Tang, B. (2017). Comparative Cost-Efficiency Analysis of Granulocyte Colony-Stimulating Factors for Use in Chemotherapy Patients in the United States. Blood 130, 4667.

Jones, C. A., London, N. R., Chen, H., Park, K. W., Sauvaget, D., Stockton, R. A., Wythe, J. D., Suh, W., Larrieu-Lahargue, F., Mukouyama, Y., et al. (2008). Robo4 stabilizes the vascular network by inhibiting pathologic angiogenesis and endothelial hyperpermeability. Nat. Med. 14, 448-453.

Korbling, M., and Freireich, E. J. (2011). Twenty-five years of peripheral blood stem cell transplantation. Blood 117, 6411-6416.

Leung, G. A., Cool, T., Valencia, C. H., Worthington, A., Beaudin, A. E., and Forsberg, E. C. (2019). The lymphoid-associated interleukin 7 receptor (IL7R) regulates tissue-resident macrophage development. Development. 146 pii: dev176180.

Miles, A. A., and Miles, E. M. (1952). Vascular reactions to histamine, histamine-liberator and leukotaxine in the skin of guinea-pigs. J Physiol 118, 228-257.

Morgan, S. J., Seymour, J. F., Grigg, A., Matthews, J. P., Prince, H. M., Wolf, M. M., and Januszewicz, E. H. (2004). Predictive factors for successful stem cell mobilization in patients with indolent lymphoproliferative disorders previously treated with fludarabine. Leukemia 18, 1034-1038.

Motta, C., Grosso, C., Zanuzzi, C., Molinero, D., Picco, N., Bellingeri, R., Alustiza, F., Barbeito, C., Vivas, A., and Romanini, M. C. (2015). Effect of Sildenafil on Pre-Eclampsia-Like Mouse Model Induced By L-Name. Reprod. Domest. Anim. 50, 611-616.

Murata, M., Harada, M., Kato, S., Takahashi, S., Ogawa, H., Okamoto, S., Tsuchiya, S., Sakamaki, H., Akiyama, Y., and Kodera, Y. (1999). Peripheral blood stem cell mobilization and apheresis: Analysis of adverse events in 94 normal donors. Bone Marrow Transplant. 24, 1065-1071.

Navarro, W. H., Switzer, G. E., and Pulsipher, M. (2013). National Marrow Donor Program Session: Donor Issues. Biol. Blood Marrow Transplant. 19, S15-S19.

Ramirez, P., Rettig, M. P., Uy, G. L., Deych, E., Holt, M. S., Ritchey, J. K., and DiPersio, J. F. (2009). BIO5192, a small molecule inhibitor of VLA-4, mobilizes hematopoietic stem and progenitor cells. Blood 114, 1340-1343.

Shaughnessy, P., Islas-Ohlmayer, M., Murphy, J., Hougham, M., MacPherson, J., Winkler, K., Silva, M., Steinberg, M., Matous, J., Selvey, S., et al. (2011). Cost and Clinical Analysis of Autologous Hematopoietic Stem Cell Mobilization with G-CSF and Plerixafor Compared to G-CSF and Cyclophosphamide. Biol. Blood Marrow Transplant. 17, 729-736.

Singh, P., Hoggatt, J., Kamocka, M. M., Mohammad, K. S., Saunders, M. R., Li, H., Speth, J., Carlesso, N., Guise, T. A., and Pelus, L. M. (2017). Neuropeptide Y regulates a vascular gateway for hematopoietic stem and progenitor cells. J. Clin. Invest. 172, 191-204.

Smith-Berdan, S., Nguyen, A., Hassanein, D., Zimmer, M., Ugarte, F., Ciriza, J., Li, D., Garcia-Ojeda, M. E., Hinck, L., and Forsberg, E. C. (2011). Robo4 cooperates with CXCR4 to specify hematopoietic stem cell localization to bone marrow niches. Cell Stem Cell 8, 72-83.

Smith-Berdan, S., Nguyen, A., Hong, M. A., and Forsberg, E. C. (2015). ROBO4-mediated vascular integrity regulates the directionality of hematopoietic stem cell trafficking. Stem Cell Reports 4, 255-268.

To, L. B., Levesque, J.-P. J.-P., and Herbert, K. E. (2011). How I treat patients who mobilize hematopoietic stem cells poorly. Blood 118, 4530-4540.

Ugarte, F., Sousae, R., Cinquin, B., Martin, E. W., Krietsch, J., Sanchez, G., Inman, M., Tsang, H., Warr, M., Passegué, E., et al. (2015). Progressive Chromatin Condensation and H3K9 Methylation Regulate the Differentiation of Embryonic and Hematopoietic Stem Cells. Stem Cell Reports 5, 728-740.

US FDA (2018). US Food and Drug Administration Pharmacology Reviews. Accessed September 2018.

One or more features from any embodiments described herein or in the figures may be combined with one or more features of any other embodiment described herein in the figures without departing from the scope of the disclosure.

All publications, patents and patent applications cited in this specification are herein incorporated by reference as if each individual publication or patent application were specifically and individually indicated to be incorporated by reference. Although the foregoing disclosure has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. A method for hematopoietic stem cell (HSC) and/or hematopoietic progenic cell (HPC) mobilization, comprising administering to a donor subject sildenafil citrate and AMD3100, and at least 1 hour after the administering, collecting the HSCs and/or HPCs from the subject, wherein the subject is not administered granulocyte-colony stimulating factor (GC SF) and wherein the sildenafil citrate is administered orally at a dose of 3 to 10 mg/kg or 30 mg/kg and the AMD3100 is administered by injection at a dose of 2.5 to 5 mg/kg.

2. The method of claim 1, wherein sildenafil citrate and AMD3100 are administered substantially simultaneously.

3. The method of claim 1, wherein sildenafil citrate and AMD3100 are administered separately.

4. The method of claim 3, wherein sildenafil citrate is administered first, followed by administering of AMD3100.

5. The method of claim 4, AMD3100 is administered at least 30 minutes after sildenafil citrate.

6. The method of claim 5, AMD3100 is administered at least 1 hour after sildenafil citrate.

7. The method of claim 3, wherein AMD3100 is administered first, followed by administering of sildenafil citrate.

8. The method of claim 7, sildenafil citrate is administered at least 30 minutes after AMD3100.

9. The method of claim 8, sildenafil citrate is administered at least 1 hour after AMD3100.

10. The method of claim 1, wherein the collecting is at least 2, at least 4, at least 6, at least 8, or at least 10 hours after the administering.

11. The method of claim 1, further comprising administering the collected HSCs and/or HPCs to a receiving subject.

12. The method of claim 11, wherein the receiving subject has or had been treated with chemotherapy.

13. The method of claim 11, wherein the receiving subject does not tolerate the mobilizing agent granulocyte-colony stimulating factor (GC SF).

14. The method of claim 11, wherein the collected HSCs and/or HPCs are used in autologous transplantation.

15. The method of claim 11, wherein the collected HSCs and/or HPCs are used in heterologous transplantation.

* * * * *